United States Patent [19]

Christen et al.

[11] 4,068,185

[45] Jan. 10, 1978

[54] CURRENT BALANCING CIRCUIT FOR USE WITH CHROMATOGRAPHIC SYSTEM DETECTOR

[75] Inventors: Urs Christen; Richard M. Commins, both of Walnut Creek, Calif.

[73] Assignee: Varian Associates, Inc., Palo Alto, Calif.

[21] Appl. No.: 662,768

[22] Filed: Mar. 1, 1976

[51] Int. Cl.² .............................................. H03F 1/34
[52] U.S. Cl. .................................... 330/86; 324/115; 324/123 C
[58] Field of Search ...................... 330/9, 86; 73/23.1; 324/115, 123 R, 123 C

[56] References Cited

U.S. PATENT DOCUMENTS 3,778,710  12/1973  Snook .................................. 330/9 X
3,936,819  2/1976  Angelle et al. ................... 324/115 X Primary Examiner—James B. Mullins
Attorney, Agent, or Firm—Stanley Z. Cole; Gerald M. Fisher; John J. Morrissey

[57] ABSTRACT

An improvement is disclosed for use in a chromatographic system of the type including detector means providing a detector output signal indicative of the level of a component sought to be determined, detector output amplifier means for receiving the signal, an error signal balancing loop connected to the amplifier output to provide a balancing signal in feedback relationship to the amplifier, and means for adjusting the sensitivity range of the amplifier. The improvement, which enables adjustment of the error signal through the feedback loop, comprises control means connected in the feedback loop for varying the sensitivity range of the amplifier in accordance with a desired mode of system operation, the control means providing a bit correction pattern for feeding into the feedback loop in accordance with the output signal of the amplifier; digital-to-analog conversion means in the loop for converting the bit stream pattern to a first resolution level; and resistor network and switching means in the feedback loop for further resolving the error signal output from the digital-to-analog conversion means, and providing the further resolved signal in feedback relationship to the amplifier to effect balancing of same.

5 Claims, 2 Drawing Figures

CURRENT BALANCING CIRCUIT FOR USE WITH CHROMATOGRAPHIC SYSTEM DETECTOR

BACKGROUND OF INVENTION

This invention relates generally to chromatographic systems and methodology, and more specifically, relates to an improved circuit for automatically balancing the detector output in a gas chromatography system.

In modern, highly automated types of gas chromatography systems, the output from the system detector is typically provided to an operational amplified which is also provided with a balancing signal. The latter functions to zero the amplifier output over its range of interest, so as to effectively establish a zero baseline, after which subsequent readout information from the chromatographic system may be properly processed. The said operational amplifier is commonly provided with a series of paralleling resistors; switching among the resistors is utilized to enable operation in different ranges of the instrument, i.e., by such switching the amplifier may be operated at various sensitivity ranges.

In a typical operation predicated on the sophisticated type of system above set forth, the output from the operational amplifier may be provided to a computer, into which the operator sets system parameters, i.e., information regarding the type of analysis being performed, the range contemplated for operation, etc. Depending upon the information set into the computer by the operator, an adjustment is enabled, automatic or otherwise, in the range of the operational amplifier, which is to say that one or another of the parallel range resistors are switched into the amplifier circuit. This action in turn, necessitates that an adjustment process be effected in the amplifier balancing each time a change is made in amplifier sensitivity. In the past this has been effected by various techniques including the use of simple manual adjustment for varying the inputs provided to the amplifier to attain a zero balance. Such techniques are obviously laborious, time consuming, and not particularly effective or repeatable.

On the other hand, more sophisticated techniques have been known for use in achieving consistent zero balancing of the aforementioned amplifier. In particular, the computer may be provided with appropriate data which can be stored at the computer memory, which data reflects the adjustments to be effected in the amplifier, i.e., in the balancing signal fed back to same, for any particular range of amplifier operation. Since the correction signal is an analog signal, this sort of corrective information must be extracted from the computer memory, routed to an appropriate latching point, and then converted into usable analog form by means of a digital-to-analog converter (DAC). This last mentioned approach while in principle capable of fully satisfactory performance, has the significant drawback of (under certain conditions) creating undue expense and complexity in the associated system. In particular, it is found in practice that in order to achieve the type of signal resolution required for typical operations, a very high bit DAC must be used. As is well known to those familiar with the present art, however, the cost of these solid state components rises rapidly with the required memory capacity, and the use of high bit DACs for the present purposes, can be virtually prohibitive in terms of cost and related complexity factors.

SUMMARY OF INVENTION

Now in accordance with the present invention, it has been found that fully effective balancing of the aforementioned detector output amplifier, and in a fully automatic automated chromatographic system environment, may be effected by utilizing a relatively low capacity memory element — in conjunction with a relatively simple technique for effecting the required further signal resolution. In particular, and in accordance with the principles of the invention, the magnitude of the balancing signal provided to the amplifier is adjusted by using the computer in conjunction with relatively low capacity memory element to scale the amplifier output; and then effecting the final required signal resolution by means of a simple resistor circuit, the precise valve of the resistance appropriate for the correction being inserted by correlating same to the sensitivity range in use at the electrometer. By use of this approach the signal resolving requirements imposed upon the memory portion of the error feedback loop, i.e. upon the DAC, is drastically reduced, thereby in turn reducing cost requirements in the overall system.

BRIEF DESCRIPTION OF DRAWINGS

The invention is diagramatically illustrated, by way of example, in the drawings appended hereto in which.

DESCRIPTION OF PREFERRED EMBODIMENT

Figure 1:
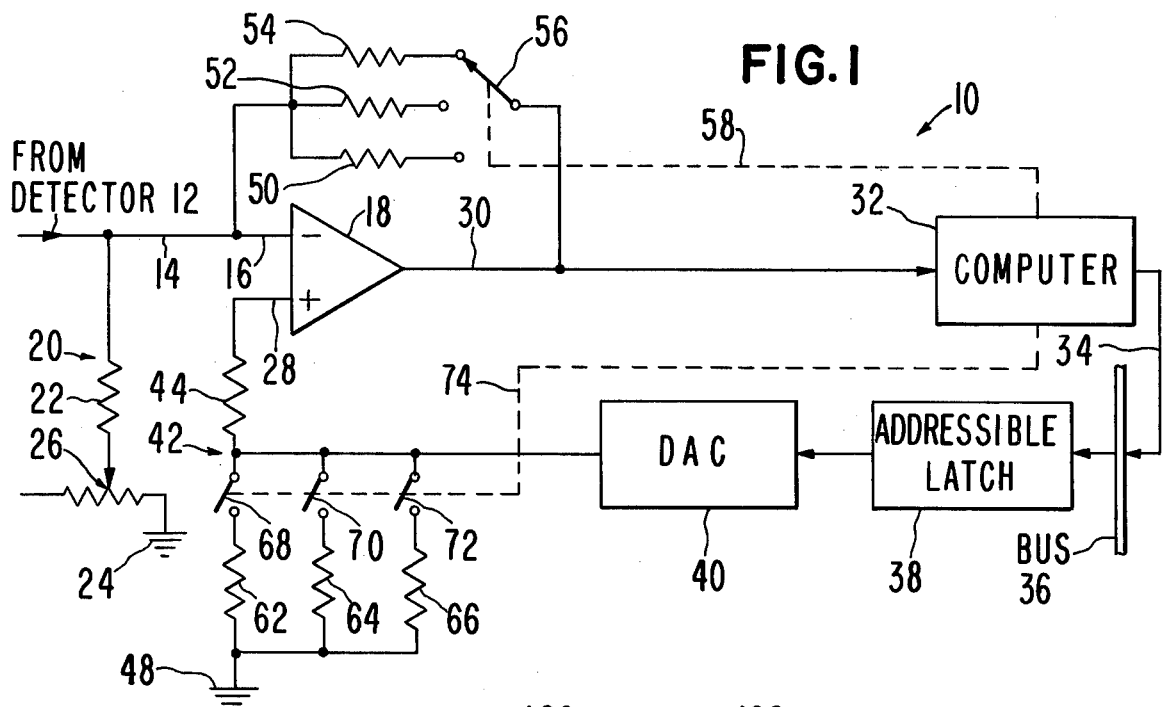
FIG. 1 is a simplified electrical schematic diagram of a circuit incorporating the principles of operation of the invention, and, FIG. 2 is an electrical schematic diagram illustrating a further circuit operating upon the principles of the present invention.

In FIG. 1 a circuit 10 is set forth incorporating the principles of operation of the present invention. The present circuit is intended primarily for use with the detector circuit of a gas chromatography system; and it may be assumed in that connection that the output provided to the circuit 10 proceeds from a detector 12, details of which are not pertinent to the present concept, except to indicate that the output from detector 12 may be indicative of concentration of a gaseous component sought to be detected in the effluent of the said apparatus — the specific detector can e.g., be of the TCD, FID, ECD types or so forth. The detector output is thus provided through line 14 to one input 16 of an operational amplifier 18. A bypass branch 20 may be provided, which includes a resistor 22, the said branch being connected to a voltage through an adjustable potentiometer 26. By suitable adjustment of potentiometer 26, it is possible to effect adjustments in the balancing of amplifier 18; and in the past this has indeed been a principal technique by which manual adjustment of such an amplifier has been effected.

The second input 28 to amplifier 18 may be provided by means of the error feedback (or balancing) loop arrangement, which includes the amplifier output 30, a computer 32, line 34 from the computer to a bus 36, an addressable latch 38 and a digital-to-analog converter (DAC) 40. The output from DAC 40 is provided to the branch 42. One side of branch 42 is connected to ground at 48, and the other end constitutes the input to amplifier 18.

Amplifier 18, as has heretofore been discussed, has associated therewith means to vary the sensitivity of same. In particular a plurality of range resistors such as resistors 50, 52 and 54 are provided. By displacement of the selector arm 56, one may choose among these resistors, which are then placed in parallel with input 16 to amplifier 18, thereby adjusting the sensitivity of such amplifier.

In the usual mode of operation of the system herein dipicted, system parameters are provided to the computer 32 i.e. the operator will set information on the computer regarding the analysis being performed. The computer by referral to appropriate memory or look-up elements, will thereupon effect adjustment of the sensitivity of amplifier 18, in particular by inserting one or another of the range resistors. This is schematically suggested by the control line 58, which can be assumed to insert the said resistors by simple solid state or electromechanical switching means such as read switches, solonoids, or by solid state equivalent elements.

It will be understood that upon the insertion of one or another of the aforementioned resistors, the operating characteristics of amplifier 18 may be changed so that together with other changes in the circuit, rebalancing of the amplifier is necessary. In point of fact the computer 32 has in the past been used to perform a relatively automatic operation of this type, by continually examining the output signal 30, i.e. at the amplifier 18 output and providing an appropriate bit correction pattern to bus 36. This bit pattern includes appropriate identification data so that an addressable latch such as at 38, can withdraw the information from bus 36 and provide same to a suitable digital-to-analog converter, which can then feed back, i.e. via the input 28, a correction signal which is precisely appropriate to assure balance of amplifier 18 at all times. It has been mentioned that this approach however, suffers from the serious drawback that the memory capacity of the DAC 40 has to be inordinate in terms of complexity — and consequent cost.

In accordance with the central aspect of the present invention, the resolution required of DAC 40 is severely curtailed. Thus in particular the elements proceeding up to and including DAC 40, i.e. the computer 32 bus 36 addressable latch 38, and DAC 40, as has been shown in the prior art, do indeed effect a scaling of output signal 30 from amplifier 18 — but it is only a scaling that is effected and not a final resolution to the required final adjusting level. That final adjusting level is enabled in the invention, by inserting in the feedback loop one or another of the resistors 62, 64 or 66. The insertion of these resistors is enabled by appropriate opening or closing of the switching means 68, 70 or 72. Control of these switches is enabled via the control line 74, which may be regarded as actuated by the same computer or similar control device 32 which effects selection among the resistors 50, 52 or 54. In other words, in accordance with the invention, a correlation is effected in the choice of the range resistor on the one hand, and in the choice of the error signal balancing resistor on the other, so that automatic compensation for the range change is in part effected by the direct and simplistic approach of inserting a corresponding resistive change in the balancing loop to the amplifier. This in turn reduces the resolution requirements imposed on DAC 40, which thus in a typical application to which the present invention appertains, may be reduced to a relatively simple eight bit unit.

The switching means 70, 72 and 74 as discussed in connection with switch 56, may comprise simple electromechanical elements, or corresponding solid state switches may be used for the purpose — with the said devices typically compassing reed switches.

Figure 2:
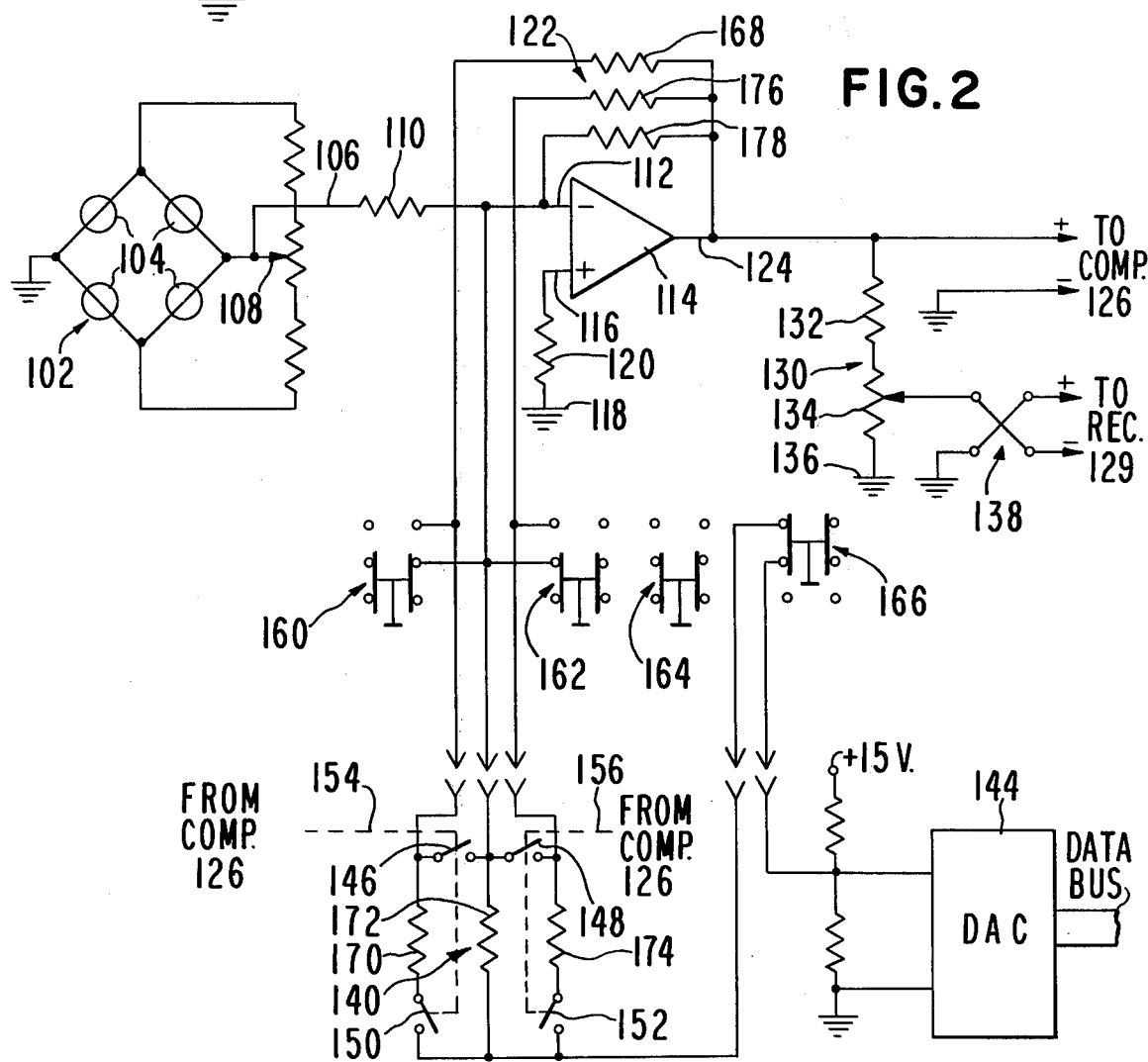

In FIG. 2 a further circuit 100 is set forth, which operates on principles substantially identical to those described in connection with FIG. 1. In this instance a detector 102 is shown, in the form of a bridge-type circuit (appropriate for a TCD type detector) with cells 104 positioned in the various branches of the circuit. As already mentioned, other detector circuits as are known in the art are equally well-suited to the invention, including FIDs and ECDs. The detector circuit output at 106 can be manually adjusted for a zero by means of the adjustable potentiometer 108. The signal after passing through a scaling resistor 110, again constitutes one input 112 of an operational amplifier 114. The operational amplifier in this instance has only one side as an input. The other input 116 is grounded at 118 through a resistor 120. A series of sensitivity adjusting resistors are again provided, indicated generally at 122. The output 124 of the amplifier is provided to a computer 126.

Also shown is input to a recorder 129, which can be taken from an attenuation branch 130, including the pair of resistors 132 and 134 connected to ground 136. Also, a polarity switch 138 is provided to assure a positive input.

In the present instance the amplifier error feedback loop adjusting resistors are generally indicated at 140. DAC 144 is in the same error signal feedback loop with these resistors. Control lines for enabling the switches 146, 148, 150 and 152 are designated at 154 and 156. These lines may be regarded as under the control of the aforementioned computer 126, and the various switches just mentioned are moved in an appropriate sequence in order to assure a similar correlation between the range sensitivity resistors 122 and the error feedback adjusting resistors 140 — as has been discussed in connection with FIG. 1.

In the present instance a series of manual range settings switches are also provided as shown at 160 through 164. These can be used to manually adjust the range; or the direct computer operation can be selected by displacement of the push button switch 166. When the latter is displaced the operation of the present circuit will be fully equivalent to that of FIG. 1. If in a given instance, for example, the range resistor 168 is inserted, the operation effected by the computer will be such as to close switches 146 and 150 with switches 148 and 152 remaining open. It will be clear that under these conditions the resistor 168 is inserted into the bypass about the amplifier, to adjust the range; and at the same time it will be evident that resistors 170 and 172 are inserted in series with the feedback loop from DAC 144.

Similarly it will be evident that upon closing of switches 148 and 152, the resistors 172 and 174 are placed in series with the feedback signal and that at the same time the resistor 176 is added to the bypass about amplifier 114, so as to adjust the sensitivity thereof. A similar correlation will seem to exist between resistor 178 and resistor 172.

While the present invention has been particularly set forth in terms of specific embodiments thereof, it will be understood in view of the present disclosure, that numerous variations upon the invention are now enabled to those skilled in the art, which variations yet reside within the scope of the present teaching. Accordingly the invention is to be broadly construed, and limited only by the scope and spirit of the claims now appended hereto.

We claim:

1. In a chromatographic system of the type including detector means providing a detector output signal indicative of the level of a component sought to be determined; detector output amplifier means for receiving said signal; and an error signal balancing loop being connected to said amplifier output to provide a balancing signal in feedback relationship to said amplifier and means for adjusting the sensitivity range of said amplifier; the improvement for adjusting the error signal through said feedback loop, comprising:

control means connected in said feedback loop for varying the sensitivity range of said amplifier in accordance with a desired mode of system operation;

said control means providing a bit correction pattern for feeding into said feedback loop in accordance with the output signal of said amplifier:

digital-to-analog conversion means in said loop for converting said bit stream pattern to a first resolution level; and resistor network and switching means in the feedback loop for further resolving the error signal output from said digital-to-analog conversion means, and providing said further resolved signal in feedback relationship to said amplifier to effect balancing of same.

2. A system in accordance with claim 1, wherein said resistor network includes a plurality of resistive paths and switching means for selecting among said paths.

3. A system in accordance with claim 2 wherein said range sensitivity means includes a series of resistive paths about said amplifier, and switching means for selecting among said paths.

4. A system in accordance with claim 3, wherein said control means effects correlation in the selection of the resistive path utilized at said sensitivity range means, and the resistive path selected at said resistor network effecting said further legal resolution.

5. A system in accordance with claim 4, wherein said control means comprises a computer.

* * * * *

UNITED STATES PATENT AND TRADEMARK OFFICE
CERTIFICATE OF CORRECTION

PATENT NO. : 4,068,185

DATED : January 10, 1978

INVENTOR(S) : Urs Christen and Richard M. Commins

It is certified that error appears in the above-identified patent and that said Letters Patent are hereby corrected as shown below:

Col. 1, line 12, "amplified" should be -- amplifier -- .

Col. 2, line 16, "valve" should be -- value -- .

Col. 5, line 8, insert a semicolon after "amplifier" .

Col. 6, line 18, "legal" should be -- signal -- .

Signed and Sealed this

Twenty-fifth Day of September 1979

[SEAL]

Attest:

LUTRELLE F. PARKER

Attesting Officer — Acting Commissioner of Patents and Trademarks